US008853261B2

(12) United States Patent
Gokaraju et al.

(10) Patent No.: US 8,853,261 B2
(45) Date of Patent: Oct. 7, 2014

(54) NUTRACEUTICAL COMPOSITION FROM GARCINIA MANGOSTANA

(75) Inventors: Ganga Raju Gokaraju, Vijayawada (IN); Rama Raju Gokaraju, Vijayawada (IN); Trimurtulu Golakoti, Vijayawada (IN); Venkateswara Rao Chirravuri, Vijayawada (IN); Kiran Bhupathiraju, Vijayawada (IN)

(73) Assignee: Laila Nutraceuticals, Vijayawada, IN (US)

( * ) Notice: Subject to any disclaimer, the term of this patent is extended or adjusted under 35 U.S.C. 154(b) by 738 days.

(21) Appl. No.: 12/863,503

(22) PCT Filed: Jan. 21, 2008

(86) PCT No.: PCT/IN2008/000040
§ 371 (c)(1),
(2), (4) Date: Jul. 19, 2010

(87) PCT Pub. No.: WO2009/093255
PCT Pub. Date: Jul. 30, 2009

(65) Prior Publication Data
US 2010/0298423 A1    Nov. 25, 2010

(51) Int. Cl.
*A61K 31/35* (2006.01)
*A61K 36/38* (2006.01)

(52) U.S. Cl.
CPC ...................................... *A61K 36/38* (2013.01)
USPC ....................................................... 514/455

(58) Field of Classification Search
USPC ....................................................... 514/455
See application file for complete search history.

(56) References Cited

U.S. PATENT DOCUMENTS

| | | | |
|---|---|---|---|
| 6,730,333 B1 | 5/2004 | Garrity | |
| 2006/0014967 A1 | 1/2006 | Sobotta | |
| 2006/0088643 A1 | 4/2006 | Fugal | |
| 2006/0105069 A1 | 5/2006 | Moffett | |
| 2006/0292255 A1* | 12/2006 | Moffett et al. | ................ 424/769 |

FOREIGN PATENT DOCUMENTS

| | | |
|---|---|---|
| CN | 1739704 A | 3/2006 |
| JP | 2003231607 A | 8/2003 |
| JP | 2003252745 A | 9/2003 |
| JP | 2005298379 A | 10/2005 |
| JP | 2008225783 A | 10/2005 |
| JP | 2006169149 A | 6/2006 |
| JP | 2006249051 A | 9/2006 |
| JP | 20061437139 A | 12/2006 |
| WO | 2006122158 A | 11/2006 |
| WO | 2007002666 A | 1/2007 |

OTHER PUBLICATIONS

Balunas et al. Xanthones from the botanical dietary supplement mangosteen (*Garcinia mangostana*) with aromatase inhibitory acitivity. J. Nat. Prod. 2008, 71, 1161-1166.*

Robinson et al., Inflammatory disease of CNS II: Meningitis and cerebral abscess, ACNR vol. 4, No. 4, Sep./Oct. 2004.
Fraenkel et al., Informed Choice and the Widespread Use of Antiinflammatory Drugs, Arthritis & Rheumatism, vol. 51, No. 2, Apr. 15, 2004, pp. 210-214.
Sastry, The Wealth of India Raw materials, vol. IV: pp. 103-105, 1956.
Martin, F. W. Durian and mangosteen. In: Tropical and Subtropical Fruits: Composition, Properties and Uses, Nagy, S.; Shaw, D. E. Eds.; AVI Publishing: Westport, CT, 1980, 407-414.
Moongkarndi et al., Antiproliferation, antioxidation and induction of apoptosis by *Garcinia mangostana* (mangosteen) on SKBR3 human breast cancer cell line, Journal of Ethnopharmacology vol. 90, Issue 1, Jan. 2004, pp. 161-166.
Peres et al., Review Tetraoxygenated naturally occurring xanthones, Phytochemistry 55 (2000) 683-710.
Peres et al., Trioxygenated naturally occurring xanthones, Phytochemistry vol. 44, Issue 2, Jan. 1997, pp. 191-214.
Asai, F., et al., A Xanthone from Pericarps of *Garcinina mangostana*, Phytochemistry, 39: pp. 943-44, 1995.
Suksamrarn, S., et al., Xanthones from the Green Fruit Hulls of *Garcinia mangostana*, J. Nat. Product., 65: 761-763, 2002.
Parveen M., et al., A Triterpene from *Garcinia mangostana*, Phytochemistry. 30: pp. 361-62, 1991.
Du C. T., et al., Anthocyanins of Mangosteen, *Garcinia mangostana*, J. Food. Science 42: pp. 1667-1669, Nov. 1977.
Holloway D. M., et al., Phenolic Compounds from the Heartwood of *Garcinia mangostana*, Phytochemistry. 14: pp. 2517-18, 1975.
Linuma, et al., Antibacterial activity of xanthones from guttiferaeous plants against methicillin-resistant *Staphylococcus aureus*. J. Pharm. Pharmacol., 48: 861-865, 1996.
Gopalakrishna C, et al., Effect of Mangostin, A Xanthone from *Garcina mangostana* Linn. In Immunopathological & Inflammatory Reactions, Indian J, Exp. Biol., vol. 18: pp. 843-846, Aug. 1980.
Gopalakrishna., G., et al., Evaluation of the Antifungal Activity of Natural Xanthones from *Garcinia mangostana* and Their Synthetic Derivatives, J. Nat. Product., 60: pp. 519-524, 1997.
Chanarat et al., Immunopharmacological activity of polysaccharide from the pericarb of *Mangosteen garcinia*: phagocytic intracellular killing activities, J Med Assoc Thai. Sep. 1997;80 Suppl 1:S149-154.
Liou et al., Gamma-pyrone compounds as potential anti-cancer drugs. J. Pharm. Pharmacol., 45(9): pp. 791-794, Sep. 1993.
Shankaranarayan et al. (1979). "Pharmacological profile of mangostin and its derivatives." Arch Int Pharmacodyn Ther 239(2): 257-269.

(Continued)

*Primary Examiner* — Jennifer M Kim
(74) *Attorney, Agent, or Firm* — Kramer Amado, P.C.

(57) ABSTRACT

Pharmaceutical, cosmetic, nutraceutical and dietary compositions derived from *Garcinia mangostana* are rich in γ-mangostin and other demethylated xanthones. These compositions exhibit potent antioxidative activity and reduce inflammation. These compositions may be used in a method of treating TNF-α, and aP2 mediated disorders. The compositions are prepared by subjecting a hydroalcoholic extract of fruit pericarp (fruit hull) of *Garcinia mangostana*, wherein said hydroalcoholic extract comprises predominantly α-mangostin, to demethylation in the presence of a Lewis acid, an organic base and a catalyst.

11 Claims, 5 Drawing Sheets

(56) References Cited

OTHER PUBLICATIONS

Nakatani et. al., Inhibition of cyclooxygenase and prostaglandin E2 synthesis by gamma-mangostin, a xanthone derivative in mangosteen, in C6 rat glioma cells. Biochem. Pharmacol, V63: pp. 73-79, 2002.

Nakatani, K., et. al., Gamma-Mangostin Inhibits Inhibitor-KB Kinase Activity and Cecreases Lipopolysaccharide-Induced Cyclooxygenase-2 Gene Expression in C6 Rat Glioma Cells. Molecular. Pharmacol 66: 667-674, 2004.

McCord et al., Superoxice Dismutase An Enzymic Function for Erythrocuprein (Hemocuprein), The Journal of Biological Chemistry, vol. 244, No, 22, pp. 6049-6055, Nov. 1969.

Lamaison, J, Petitjean-Freytet, C., Carnet, A., 1991. Lamiacees Medicinales a Proprietes Antioxydantes, Sources Potentielies d'acide Rosmarinique. Pharm. Acta Helv. 66:185-188.

Schewe et at, Enzymology and Physiology of Reticulocyte Lipoxygenase: Comparison with Other Lipoxygenases, Adv Enzymol, vol. 58; pp. 191-272 (1986).

Reddanna et al., Purification of Arachidonate 5-Lipoxygenase from Potato Tubers, Biosynthesis, Enzymology, and Chemical Sythesis, Methos in Enzymology, vol. 187, pp. 268-277, 1990.

* cited by examiner

NUTRACEUTICAL COMPOSITION FROM *GARCINIA MANGOSTANA*

FIELD OF THE INVENTION

The invention relates to enriched compositions of γ-mangostin and other demethylated xanthones and the process for preparation thereof. These enriched fractions exhibit potent antioxidative activity and reduce inflammation. The present invention further relates to nutraceutical compositions, dietary supplements, pharmaceutical formulations and cosmetic preparations comprising the said enriched compositions. The said enriched compositions are evaluated for their antioxidant activity, anti-inflammatory activity and 5-lipoxygenase inhibitory activity.

BACK GROUND OF THE INVENTION

Inflammation is a complex protective biological process triggered by irritation, injury or infection, characterized by redness, heat (due to increased blood flow), swelling (due to increased vascular permeability), loss of function and pain (due to sensitization of pain receptors). In addition to the foregoing induced conditions, inflammation can also occur due to age related factors. Chronic inflammatory condition and cancer have become emerging health concerns in a number of countries across the globe. Inflammation has proven to be part of etiology of several chronic diseases like vasculitis, atherosclerosis, ulcerative colitis, inflammatory bowel syndrome, diabetes, Alzheimer's, Meningitis etc., (Susan Robinson & William Stewart, Inflammatory disease of CNS II: Meningitis and cerebral abscess, ACNR volume 4 number 4 September/October 2004).

Non-steroidal anti-inflammatory drugs are most commonly used remedies for inflammatory diseases. Phytochemicals from certain plants were reported to demonstrate anti-inflammatory properties. Like aspirin many are presumed to work by blocking cyclooxygenase, lipoxygenase and phospholipase. Presently, there has been a tremendous surge in demand for natural non-steroidal anti-inflammatory drugs (NSAIDs) because of their established safety and efficacy, through decades of usage by various cultures (Liana Fraenkel, et. al, Arthritis & Rheumatism, Vol. 51 (2): pp 210-214, 2004).

*Garcinia mangostana* L belongs to Guttiferace family. It is commonly known as Mangosteen. Mangosteen is a slow-growing topical, evergreen tree and can attain 6-25 m in height with leathery glabrous leaves (B. N. Sastry, The Wealth of India Raw materials, Vol. IV: pp 103-105, 1956). The tree is mainly found in India, Myanmar, Sri Lanka and Thailand. The edible fruits of this plant are considered to be one of the best of all tropical fruits. The edible fruits are white, soft and juicy with a sweet, slightly acrid taste and pleasant aroma (F. W. Martin., Durrian mangosteen. In tropical and Subtropical fruits: Composition properties and uses; S. Nagy., D. E Shaw., Eds: AVI publishing Westport. Conn., pp 407-414, 1980). The fruit hull of the mangosteen has been used in Thai folk medicine for treatment of skin infection, wounds and diarrhea for many years (Moongkarndi, P., et. al., *J. Ethanopharmacol.* 90: pp 161-186, 2004)

In the ayurvedic system of medicine, the fruit hull of the plant finds wide application, mainly as an anti-inflammatory agent and in the treatment of diarrhea (V. Peres, et. al., *Phytochemistry* 55: pp 683-710, 2000; V. Peres et. al., *Phytochemistry*. 44: pp 191-214, 1997).

Phytochemical investigations of the plant *Garcinia mangostana* have resulted in the isolation and identification of a variety of secondary metabolites, such as oxygenated and prenylated xanthones (Asai, F., et al., *Phytochemistry,* 39: pp 943-44, 1995; Siksamran, S., et al., *J. Nat. Product.,* 65: 761-763, 2002), triterpenoids (Praveen M., et al., *Phytochemistry.* 30: pp 361-62, 1991), anthocyanin glycosides (Du C. T., et al., *J. Food Science* 42: pp 1667-1669, 1977) and benzophenone derivatives (Holloway D. M., et al., *Phytochemistry.* 14: pp 2517-18, 1975). These oxygenated and prenylated xanthones have demonstrated various biological activities such as antibacterial (Linuma M., et al., *J. Pharm. Pharmacol.,* 48: pp 861-865, 1996), anti-inflammatory (Gopalakrishna C., et al., *Indian J, Exp. Biol.,* 18: pp 843-846, 1980), anti fungal (Gopalakrishna., G., et al., *J. Nat. Product.,* 60: pp 519-524, 1997), immunomodulating (Chanarat P., et al., *J. Med. Asso. Thai.,* 80: S149-154, 1997), anti-cancer (Liou S. S., et al., *J. Pharm. Pharmacol.,* 45: pp 791-794, 1993) and other pharmacological activities (Shankaranarayana D., et al., *Arch Internat, Pharmaco. Therapie.,* 239: pp 237-269, 1979).

Xanthones were identified to be the active principles responsible for Mangosteen's anti-inflammatory properties. The mangostin compounds were found to inhibit both 5-lipoxygenase and cycloxygenase-2 enzymes (Nakatani, K., et. al., Biochem. Pharmacol, V63: pp 73-79, 2002). α-Mangostin and γ-Mangostin are the most prominent among more than a dozen xanthone compounds called mangostins isolated from *Garcinia* mangosteen. γ-Mangostin directly inhibits IKK activity, which specifically phosphorylates IθB, and thereby prevents its degradation and, as a result, induces a decrease in the expression of COX-2 protein and its mRNA by a suppression of NF-κB-dependent transcription. (Nakatani, K., et. al., Biochem. Pharmacol, V66: pp 667-674, 2002).

The US patent application 20060014967 relates to a process for obtaining and purifying pure .alpha.-mangostin from the rind of the fruit (mangosteen) of *Garcinia mangostana.*

CN1739704A relates to a Chinese medicine oral liquid formulation for treating tonsillitis, comprising pinellia tuber, balloon flower root, licorice, Indian trumpet flower seed, mangosteen, fresh pear and honey in certain proportion. This invention was reported to have total effective rate of 100% in treating various kinds of tonsillitis.

WO06137139A1 provide a method of isolating a mangosteen derivative whereby the mangosteen derivative having various pharmacological effects can be efficiently purified by using a highly safe solvent, and a drug and a health food containing the mangosteen derivative having a high safety.

JP2006249051A2 describe a fibroblast-activator containing mangosteen with high effectiveness and safety, and a skin lotion containing the activator as an active ingredient and exhibiting a marked effect in skin aging prevention and the prevention/improvement of symptoms of skin roughness JP2006169149A2 present an epidermal basal cell-growth promoter of skin containing an extract of *Garcinia mangostana*_Linne. The epidermal basal cell-growth promoter of skin contains an extract of *Garcinia mangostana* Linne., as an active ingredient obtained by immersing fruit of *Garcinia mangostana* Linne. in water and an organic solvent.

US20060088643A1 describes a neutraceutical beverage comprising pericarp extract from the *Garcinia mangostana* L. (mangosteen) plant, and juice from mangosteen fruit pulp, preferably combined with juice from at least one of four other ingredients selected from red grapes, lycium, sea buckthorn, and apple, preferably obtained from powdered extract of mangosteen pericarp and a mixture of fruit concentrate and/or powdered fruit and/or fruit extract.

U.S. Pat. No. 6,730,333 presents a nutraceutical compositions derived from the fruit of the *Garcinia mangostana* L. or mangosteen plant are provided. The nutraceutical mangosteen compositions employ novel combinations of mangosteen fruit pulp and pericarp, and can be additionally complemented by selected juice concentrates to yield a composition for improving general health and wellness in humans.

JP2003231607A2 presents a mangosteen extract which does not exhibit a deep color/color deepening by oxidation during extraction, cleaning, drying and processing processes and has excellent antimicrobial and deodorizing action in a low concentration on offensive smell/malodor caused by proliferation of harmful microorganisms, and an antimicrobial deodorant containing the same.

WO06122158A2 describe skin care compositions containing xanthones extracted from plants are described. These compositions include lotions, creams, ointments, and the like that reduce wrinkles, give skin a more youthful appearance, provide antioxidant effects, protect the skin, and moisturize the skin. The compositions contain an admixture of a base and a xanthone-containing plant extract.

JP2005298379A2 describe an IκB kinase inhibitor inhibiting IκB kinase (a) causing NF-κB activation causing transcriptional enhancement of genes relating to immunity, inflammatory reaction, cell growth control and apoptosis, comprising at least one selected from extracts, extracted from fruits or pericarps of a mangosteen (*Garcinia mangostana* L.), α-mangostin and γ-mangostin is provided, and a composition containing the inhibitor is provided.

JP08225783A2 describes an antioxidant containing an extract separated from the pericarp of a mangosteen as an active ingredient. The active ingredient is obtained by pulverizing the dried mangosteen, then carrying out the cold leaching with methanol, subsequently partitioning and extracting the methanol extraction essence with acetic acid and water at 1:1 ratio, then treating a part passed into the ethyl acetate by a silica gel chromatography, eluting the resultant extract with n-hexane-ethyl acetate (at 3:1 ratio) and thereby providing the extract as a fraction containing γ-mangostin of the formula.

JP2003252745A2 provide a matrix metalloproteinase (MMPs) inhibitor capable of preventing the aging of the skin by inhibiting activities of the MMPs belonging to a gelatinase group, a stromeleicin group or a collagenase group which give a large effect on the aging of the skin. The matrix metalloproteinase inhibitor comprises one or more kinds of compounds of catechins, procyanidins and mangosteens.

WO07002666A2, US20060292255A1 and US20060105069A1 relates to pharmaceutical, therapeutic, nutritional, cosmetic, and dermatological compositions derived from the pericarp (rind) of the *Garcinia mangostana* L plant and the extraction processes used to produce those compositions. This patent application describes compositions comprising an approximately 0.01% to about 80% mixture of a xanthone-rich mangosteen pericarp (rind) extract in novel combinations for pharmaceutical, cosmetic, therapeutic or dermatological compositions that yield surprising health benefits.

Out of all the known mangostin compounds (FIG. I) isolated from *G. mangostana*, the most prominent xanthone, α-mangostin is in the range of 20-25% and minor γ-mangostin is in the range of 3-5% in the alcohol extract. All the process patents described above relates to general enrichment of total mangostin compounds exist in the *Garcinia mangostana* fruit pericarp. The products of the above processes contain α-mangostin as a major component and γ-mangostin as one of the minor components. None of the prior art relates to the selective enrichment of γ-mangostin from the natural mangostin composition derived from *Garcinia mangostana*.

The US20060292255A1 patent describes the compositions derived from mangostin compounds from the fruit extract and the process steps described therein can lead to general enrichment of all mangostin compounds. However, the specification of this patent inadvertently claims the enrichment of γ-mangostin upto 40%, though no selective enrichment of γ-mangostin has been attempted or described. The physical and chemical properties of the γ-mangostin and α-mangostin are closely similar. As such the process described therein, which involves merely a base treatment and partitions, could not have achieved the selective enrichment of γ-mangostin over α-mangostin. Rather the product of this invention should be a composition enriched in total mangostins comprising α-mangostin as the major xanthone. Enriching the γ-mangostin to phytochemical purity from the 3-5% natural concentration commonly available in the extract, through a process involving column chromatography, as described in patent JP08225783A2 for identification and bio-activity study purposes is not economical for bulk enrichment or commercial utility. The commercial preparation of compositions prominent in γ-mangostin is not feasible without the intervention of non-conventional enrichment techniques.

There exists a need for improved nutraceutical composition that offers the health benefits of *Garcinia mangostana* and comprises prominently the most active compounds.

It is therefore an object of the present invention to provide an improved non-toxic dietary supplement composition, which prevents or improve the disease conditions associated with 5-lipoxygenase, inflammatory diseases like rheumatoid arthritis, periodontal disease, asthma, bowel disease such as ulcerative colitis, circulatory disorders such as shock and ischemia, free radical mediated disorders such as cancer, Alzheimer and Parkinson's and cardiovascular disease.

SUMMARY OF THE INVENTION

The present invention discloses new dietary/nutraceutical/pharmaceutical/cosmetic compositions derived from *Garcinia mangostana* and more particularly the present invention relates to efficacious dietary/nutraceutical compositions.

The major objective of the present invention is to provide dietary/nutraceutical/pharmaceutical/cosmetic compositions selectively enriched in γ-mangostin for improved therapeutic effect.

Further objective of the present invention is to provide a method for making xanthone compositions enriched in γ-mangostin from *Garcinia mangostana*.

The primary objective of the present invention is to provide a dietary/nutraceutical composition that contributes to general human wellness and good health through improved composition.

An additional object of the present invention is to provide an improved treatment for 5-lipoxygenase and TNF-α mediated disease conditions including asthma, free radical mediated diseases, and as an antibiotic comprising administering an effective amount of the improved composition derived from *Garcinia mangostana*.

Yet another object of the present invention is to provide a commercial process for the manufacture of improved dietary/nutraceutical composition of *Garcinia mangostana* plant.

It also an object of the present invention to provides a non asthma aggravating anti-inflammatory product which can reduce leukotriene biosynthesis and ameliorate air way inflammation during bronchial asthma.

DETAILED DESCRIPTION OF THE INVENTION

Figure 1:
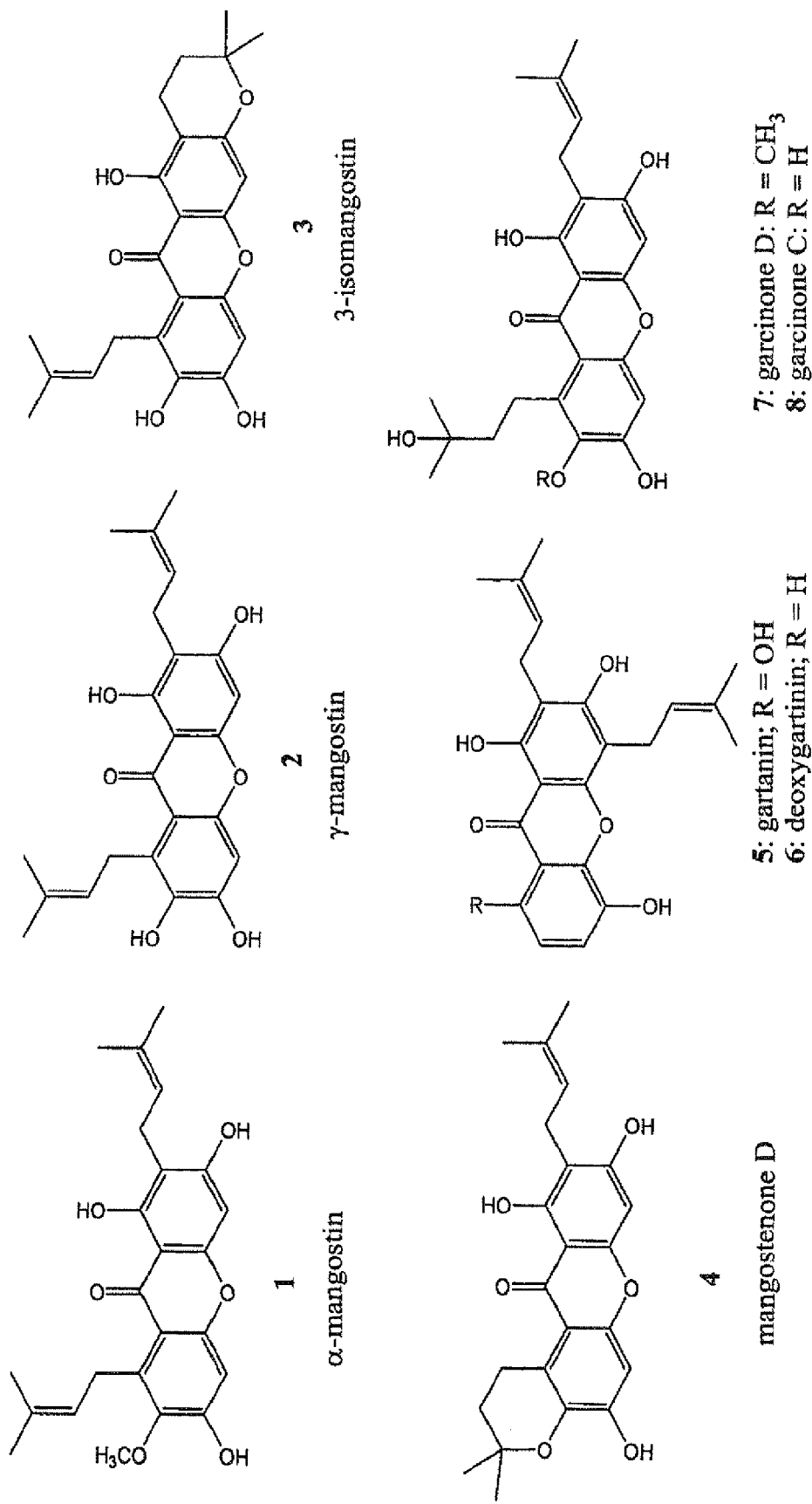
FIG. 1, hereinafter referred to as Figure I, presents the chemical structures of major xanthones isolated and characterized from *Garcinia mangostina*
Figure 2:
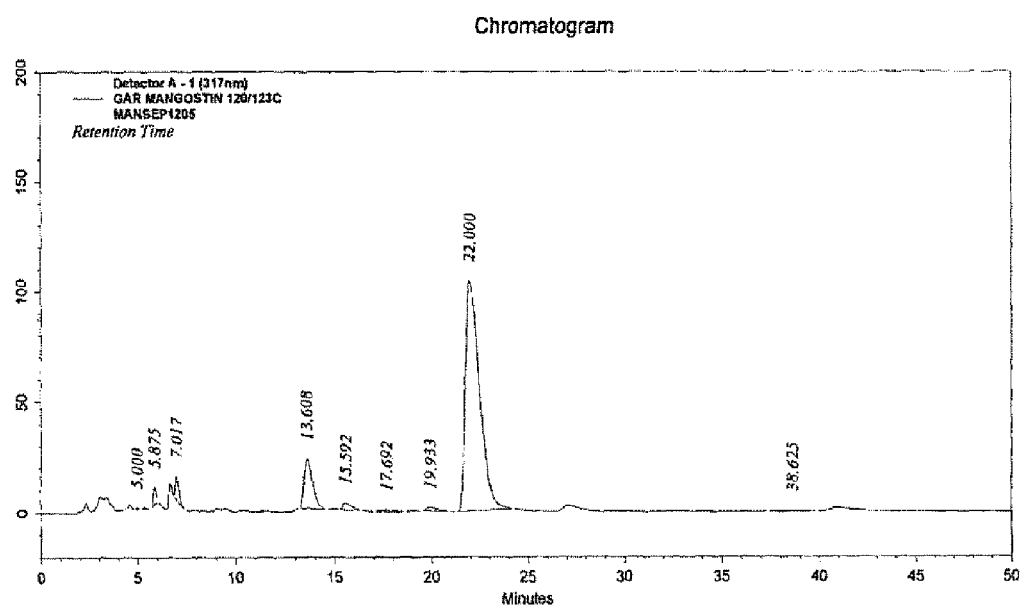
FIG. 2, hereinafter referred to as Figure II, presents chromatographic representation of xanthone compounds present in the natural extract of *Garcinia mangostana* fruit rind obtained by extraction with 90% methanol.
Figure 3:
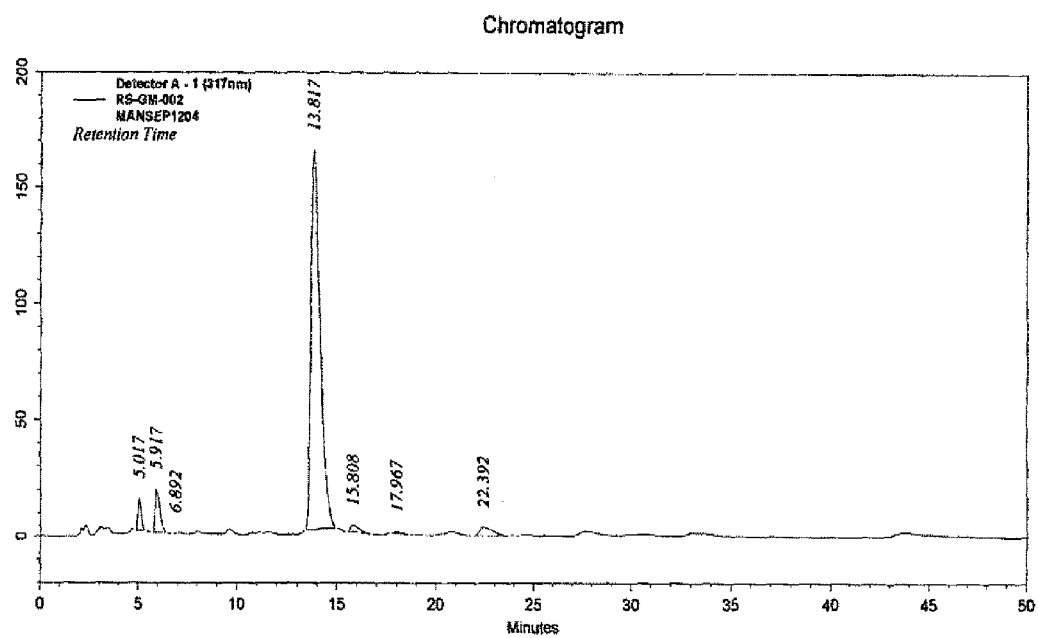
FIG. 3, hereinafter referred to as Figure III, presents chromatographic representation of xanthone compounds present in the enriched extract of *Garcinia mangostana* fruit rind obtained by demethylation of 90% methanol extract.
Figure 4:
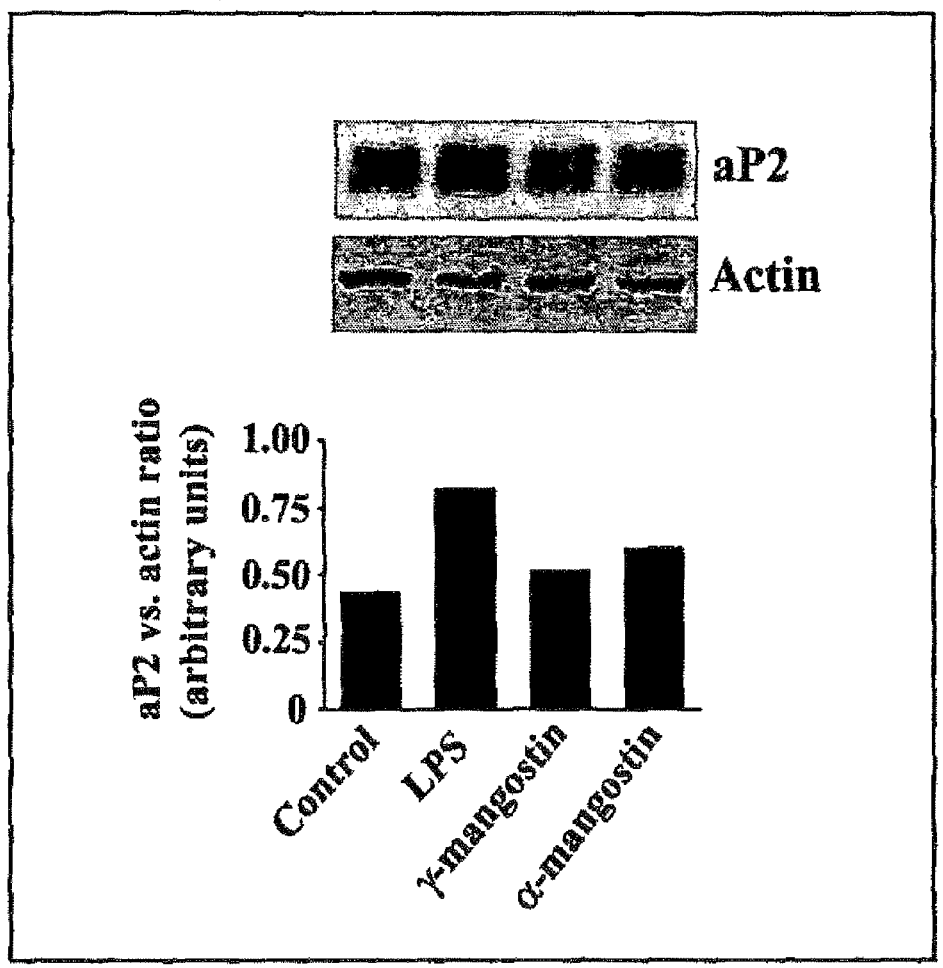
FIG. 4, hereinafter referred to as Figure IV, shows the anti-asthma activity of mangostin compounds. The Western-immunoblots normalized with the expression of actin, depicting the modulation of expression of adipocyte fatty acid-binding protein (aP2) protein by γ-mangostin or α-mangostin in human monocytes THP-1 cells derived macrophages.
Figure 5:
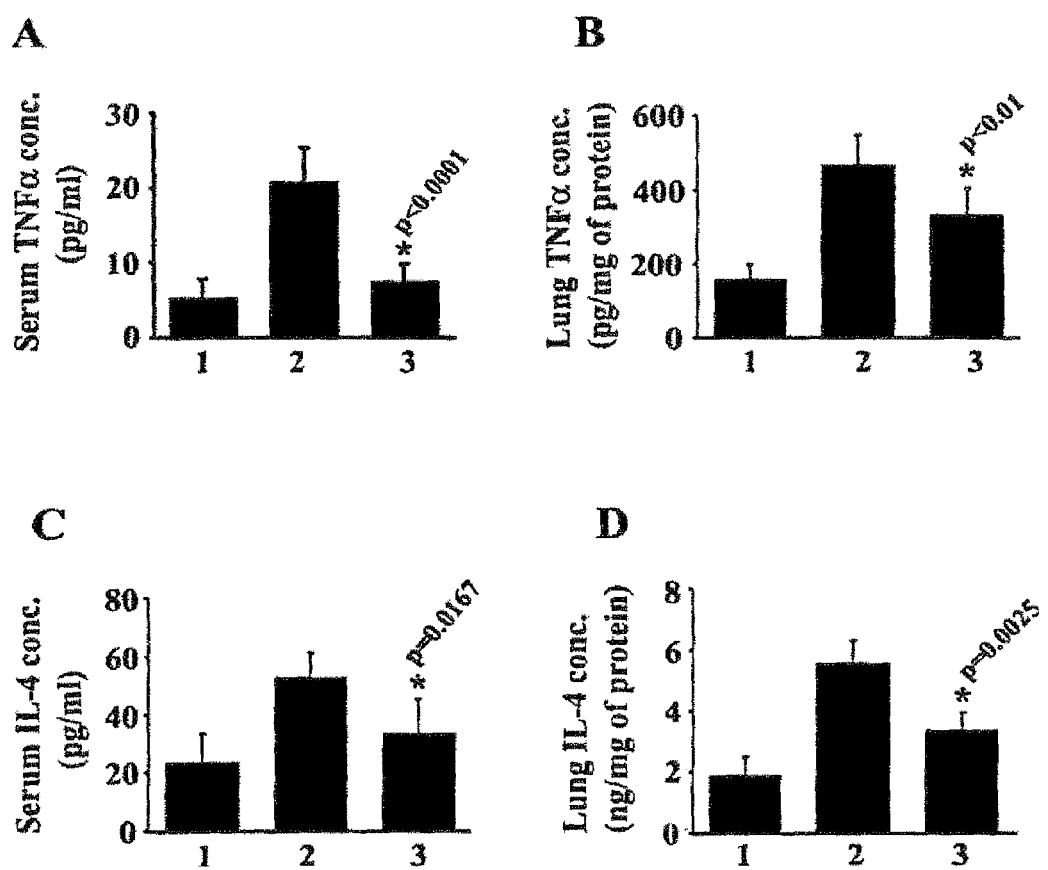
FIG. 5, hereinafter referred to as Figure V, shows reduction of TNFα (A & B) and IL-4 (C & D) in Sprague-Dawley rats with airway inflammation induced by Sephadex LH-20 after supplementing the study animals with composition-I, compared to vehicle control group and untreated airway inflammation induced (Sephadex induced) control group. TNFα and IL-4 concentrations were measured in serum (A & C) and lung tissue lysates (B & D) by specific antibody coated ELISA plates. Experimental protocol includes a vehicle control group (1) inoculated with saline in naïve animals, untreated asthma control group (2), wherein airway inflammation is induced by intratracial inoculation of Sephadex in CMC, and the treatment group (3) supplemented with 50 mg/kg/day composition-I for ten days prior to inducing airway inflammation by intratracial administration of Sephadex in CMC. Each bar represents mean±SD (n=6). T-test values are indicated on the bars, compared with the Sephadex induced group.

The invention will now be described in detail in connection with certain preferred and optional embodiments, so that various aspects thereof may be more fully understood and appreciated.

The inflammatory and carcinogenesis processes are known to be triggered by increased metabolic activity of arachidonic acid. Arachidonic acid diverges down into two main pathways during this process, the cyclooxygenase (COX) and lipoxygenase (LOX) pathways. The COX pathways lead to prostaglandins and thromboxane production and the LOX pathways leads to leukotrienes (LTS) and hydroxyl eicosatetraenoic acid (HETEs). These classes of inflammatory molecules exert profound biological effects, which enhance the development and progression of human cancers. Inhibition of 5-lipoxygenase indirectly reduces the expression of TNF-α.

Both 5-Lipoxygenase and TNF-α, therefore, are the target enzymes useful for identifying inhibitors, which have the potential to cope with a variety of inflammations and hypersensitivity-based human diseases including asthma, arthritis, bowel diseases such as ulcerative colitis and circulatory disorders such as shock and ischemia.

Asthma is a complex chronic inflammatory disease of the airways that involves the activation of many inflammatory and structural cells, all of which release inflammatory mediators that result in the typical patho-physiological changes. Cytokines play an integral role in the coordination and persistence of the inflammatory process in the chronic inflammation of the airways in asthma. They are capable of inducing many of the pro-inflammatory effects characteristic of this disease and are being recognized as important targets for treatment. Among these, pro-inflammatory cytokines such as TNFα, IL-1β, IL-6, GM-CSF and Th2 subset derived IL-4, IL-5 and IL-13 lymphokines are considered as the key factors of pathogenesis of asthma.

Furthermore, in recent studies, involving adipocyte fatty acid-binding protein (aP2)-deficient mice model of allergic airway inflammation, have proven that infiltration of leukocytes, especially eosinophils into the airways was highly dependent on aP2 function. In addition, T cell priming was unaffected by aP2 deficiency, suggesting that aP2 plays an important role in regulation of immune responses in bronchial epithelial cells, the site of allergic manifestations in asthma.

Based on the above information, the inventors have conducted several enzymatic and cell based in vitro anti-inflammatory studies on pure phytochemicals and fractions derived from *Garcinia mangostana*. These studies have un-expectedly indicated that γ-mangostin (structure 2; FIG. I) is the most active xanthone biologically against 5-lipoxygenase enzyme ($IC_{50}$ 0.52 µg/mL; table 3) and TNF-α (a cytokine that plays a key role in inflammation, $IC_{50}$ 3.32 µg/ml; table 4). The major xanthone in the natural extract, α-mangostin (1), however showed the $IC_{50}$ values, 2.7 µg/mL and 9.5 µg/mL respectively against 5-lipoxygenase and TNF-α. The γ-mangostin is O-demethyl analog of α-mangostin. Another O-demethylxanthone, garcinone C (8) also showed relatively higher potency compared to its natural O-methyl counterpart, garcinone D (7).

The inventors also assessed the effect of α-mangostin and γ-mangostin on adipocyte fatty acid-binding protein aP2 expression in human monocytes-macrophage cells in a cell based in vitro model. In this experiment, THP-1 human monocyte-macrophage cells were pre-treated with 5 µg/ml of γ-mangostin or α-mangostin for 2 h and thereafter primed with LPS to induce the inflammatory response. The cellular proteins were extracted by cell lysis buffer and subjected to immuno-western blot to detect the modulation of expression of aP2 protein. The data has shown un-expectedly that γ-mangostin inhibited the LPS induced aP2 expression more strongly compared to α-mangostin (FIG. IV).

The forgoing studies have established for the first time that γ-mangostin is superior as a potential inhibitor of 5-lipoxygenase enzyme, TNF-α and aP2 expression. The extracts or composition affluent in γ-mangostin should therefore provide improved efficacy.

Hence, the main objective of the present invention is to develop compositions highly enriched in γ-mangostin. The compositions described in the prior art contain α-mangostin as the major compound. The extract of fruit pericarp of *Garcinia mangostana* contains a natural composition comprising α-mangostin in the range of 20-30% and minor γ-mangostin in the range of 3-5% along with the other minor compounds as summarized in table 1 and depicted by FIG. I and by the HPLC chromatogram in FIG. II. However, from the foregoing, the compositions containing γ-mangostin as a major ingredient together with other O-demethyl xanthones are the most desirable therapeutically. The composition containing γ-mangostin as the major active ingredient will also have greater commercial potential. The process for the preparation of compositions selectively enriched in γ-mangostin was not attempted yet in the prior art, except a conventional purification of minor quantity of γ-mangostin naturally exists in the extracts. Especially the enrichment of γ-mangostin through a simultaneous suppression of less active α-mangostin was not reported in the prior art. This lacuna, which was not addressed by any prior art patents or literature articles, has been the subject matter of the present invention.

Therefore, in a preferred embodiment, the invention provides a pharmaceutical/nutraceutical/cosmetic/dietary supplement compositions with enhanced anti-oxidative and anti-inflammatory activity obtained by selective enrichment of γ-mangostin from *Garcinia mangostana* pericarp comprising γ-mangostin in the range of 20% to 95%, α-mangostin in the range 0 to 5%, garcinone C in the range of 0.1-4% and 3-isomangostin in the range of 0.1-5% of total weight of composition along with suitable pharmaceutical carriers/excipients and a process for the preparation of the same.

In another preferred embodiment, the invention provides a pharmaceutical/cosmetic/nutraceutical/dietary supplement composition, which comprises γ-mangostin in the range of 20% to 40% of total weight of composition, α-mangostin in the range 0 to 3%, garcinone C in the range of 0.5 to 3% and 3-isomangostin in the range of 0.5 to 2.5%.

In a further embodiment, the invention provides a pharmaceutical//cosmetic/nutraceutical/dietary supplement composition which comprises γ-mangostin in the range of 40% to 70% of total weight of composition, α-mangostin in the range 0 to 4%, garcinone C in the range of 0.5 to 4% and 3-isomangostin in the range of 0.5 to 4%.

In yet another preferred embodiment, the invention provides a pharmaceutical//cosmetic/nutraceutical/dietary supplement composition which comprises γ-mangostin in the range of 85% to 95% of total weight of composition, α-mangostin in the range 0 to 1%, garcinone C in the range of 0.1 to 2% and 3-isomangostin in the range of 0.1 to 2%.

The above composition may also contain 0 to 5% of other mangostin compounds generally found in the natural extracts.

The present invention demonstrates an improved composition selectively enriched in γ-mangostin from *G. mangostana*, with superior 5-lipoxygenase and TNF-α inhibitory activities (table 2) compared to the natural extract prominent in α-mangostin. The enriched composition was obtained by selective enrichment of natural O-demethyl xanthones especially γ-mangostin through a conversion of α-mangostin and other O-methylated xanthones through a process called O-demethylation.

The present invention also relates to a process for preparation of improved compositions from *G. mangostana*, the said process comprises of extracting dried and powdered fruit rind of *Garcinia mangostana* with polar solvent selected from a group consisting of water, alcohol, ketones and any mixture thereof. The solvent was evaporated and the extract was subjected to demethylation using Lewis acid catalyst in a suitable solvent medium to obtain a composition selectively enriched in γ-mangostin.

Accordingly, a process for producing a fraction enriched in γ-mangostin and other demethylated xanthones comprises the steps of:

a) subjecting the hydroalcoholic extract of the fruit pericarp (fruit hull) of *Garcinia mangostana*, comprising prominently α-mangostin, in addition to the other minor xanthones, to demethylation in presence of a Lewis acid and organic base and a catalyst in an organic solvent to yield a composition (composition-I) enriched in demethylated xanthones, comprising γ-mangostin in the range of 20% to 40% of total weight of the composition, α-mangostin in the range of 0 to 3%, garcinone C in the range of 0.5 to 3% and 3-isomangostin in the range of 0.5 to 2.5%;

b) dissolving the above demethylated mangostin extract enriched in γ-mangostin in aqueous organic solvent and adjusting the pH to 10-10.5 with alkali solution followed by subjecting the mixture to a resin column chromatography (styrene-divinylbenzene resin, R 20), by eluting the column with water, followed by an organic solvent, evaporating the organic solvent eluted fraction to obtain composition-II, comprising γ-mangostin in the range of 50% to 70% of total weight of composition, α-mangostin in the range of 0 to 4%, garcinone C in the range of 0.5 to 4% and 3-isomangostin in the range of 0.5 to 4%;

c) dispersing the said composition (composition-II) into dichloromethane, stirring the solution for 30 min followed by filtration of the insoluble solid material, drying the solid under vacuum to obtain composition-III comprising γ-mangostin in the range of 85% to 95% of total weight of composition, α-mangostin in the range 0 to 1%, garcinone C in the range of 0.1 to 2% and 3-isomangostin in the range of 0.1 to 2%.

The Lewis acid catalysts are selected from a group consisting of aluminum chloride, aluminum bromide, aluminum iodide, boron tribromide or boron trichloride-methyl sulfide complex or sodium salt of N-methylaniline or sodium ethanethiolate or lithium chloride in dimethyl formamide or beryllium chloride. The Lewis acid used is preferably selected from the group consisting of aluminum chloride, aluminum bromide, aluminum iodide and beryllium chloride.

An organic base and a catalyst are used for demethylation, in addition to aluminium halides. Organic bases are selected from a group consisting of pyridine, triethylamine, piperidine and the catalyst is selected from alkali metal iodide or PTC catalyst such as tetrabutylammonium bromide.

The alkali metal iodide is selected from a group comprising sodium iodide, potassium iodide, magnesium iodide, calcium iodide and the like.

Solvents for conducting the demethylation is selected from chloroform, dichloromethane, 1,2-dichloroethane, 1,3-dichloropropane and tetrahydrofuran or mixtures thereof.

The γ-mangostin enriched composition (composition-I) is alternatively subjected to silica gel/reversed phase flash column chromatography to yield a fraction enriched in γ-mangostin in the range of about 50 to 70%.

The γ-mangostin enriched composition (composition-II) is subjected to column chromatography over silica/reversed phase silica followed by crystallization to yield a composition comprising γ-mangostin in the range of 85-95%.

The organic solvent used in step (b) is selected from a group consisting of acetone, methanol, ethanol, isopropanol or mixtures thereof.

In another preferred embodiment, the invention provides a pharmaceutical composition or dietary supplement for use in treating inflammatory diseases, cancer and diseases caused by microbial infection which comprises a therapeutically effective amount of one of the enriched γ-mangostin composition in admixture with one or more pharmaceutically acceptable excipients.

In yet, another embodiment, the invention provides a method for treating inflammatory diseases, cancer and free radical mediated diseases including Parkinson's and Alzheimer's which comprises administering to a mammal in need of such treatment a therapeutically effective amount of γ-mangostin enriched composition of the invention.

The present inventive composition comprises γ-mangostin in the range of 20-40% and α-mangostin in the range of 0-2% along with other minor xanthones as summarized in table 1 and depicted by HPLC chromatogram in FIG. III. In particular, the selectively enriched powder extract derived from *Gar-*

*cinia mangostana* provides improved composition for use in treating inflammation in patients prophylactically and/or therapeutically.

In a preferred process, *G. mangostana* fruit rind was dried, ground to coarse powder and extracted with 90% methanol at 60-65° C. The solvent was removed by filtration and the extraction process repeated thrice using the same solvent and the combined solution was fine filtered and evaporated under reduced pressure. The crude extract was dissolved in 1,2-dichloroethane and subjected to O-demethylation at reflux temperature using $AlCl_3$/pyridine and sodium iodide catalyst. After 2 h, the reaction mixture was poured into mixture of 3N HCl and brine solution and extracted with THF. The organic layer was washed with brine, dried over anhydrous $Na_2SO_4$, treated with triethylamine and concentrated into syrup containing 40% total solids under vacuum and the crude mixture was poured into ice water. The precipitate was filtered, washed with water and dried in a vacuum oven to obtain the composition-I enriched in γ-mangostin. The mixture was analyzed by HPLC (FIG. III). The composition-I contain 3-isomangostin in the range of 0.5-2.5%, Garcinone C in the range of 0.5-3%, Garcinone D in the range 0-0.1%, γ-Mangostin in the range of 20-40%, Deoxygartanin in the range of 0.5-1%, Gartanin in the range of 0.5-2%, α-Mangostin in the range of 0-3%.

The fraction was enriched to possess upto 40-50% γ-mangostin by conducting the demethylation step on a mangostin extract prior enriched to contain 40-50% α-mangostin or by washing powdered composition-I thoroughly with ethyl acetate on a Buckner funnel.

The 5-lipoxygenase inhibitory activity of the enriched extract was measured and compared with the natural extract (table 3). The γ-mangostin enriched extract containing 35% γ-mangostin infact showed better 5-lipoxygenase activity ($IC_{50}$ 1.5 µg/mL) compared the natural extract containing 34% α-mangostin ($IC_{50}$ 3.8 µg/mL). The improved efficacy of the γ-mangostin enriched extract was also supported by its in vivo activity against an inflammatory disease called asthma as depicted in FIG. V. The airway inflammation was induced in Sprague-Dawley rats through intratracheal inoculation of Sephadex LH-20 compound as a suspension in sterile saline. The treatment group was supplemented with 50 mg/kg/day γ-mangostin enriched extract (composition-I) for 10 days prior to the induction of airway inflammation. An untreated group was also subjected to Sephadex inoculation to induce airway inflammation and it was taken as control group. Another untreated group was inoculated with sterile saline intratracheally and designated as vehicle control group. All the animals were sacrificed 24 h after the Sephadex challenge. The serum and lung tissue were extracted and subjected to TNFα and IL-4 biomarker analysis by specific antibody coated ELISA plates.

The untreated but airway inflammation induced control group showed significant increase in serum and lung tissue TNFα (A2 & B2) and IL-4 (C2 & D2) concentration compared those in saline (vehicle) inoculated naïve animals group (A1 & B1) and (C1 & D1), confirming the induction of airway inflammation in Sephadex inoculated group. The TNFα (A3 & B3) and IL-4 (C3 & D3) concentrations in serum and lung tissue in the treatment group of animals supplemented with γ-mangostin enriched extract (composition-I) were reduced close to those in the naïve group indicating the amelioration of inflammatory condition in the animals supplemented with composition-I.

The composition-I also showed potent antimicrobial activity. As such the enriched compositions can be used in cosmoceutical formulations.

The composition can be further enriched to contain upto 50-70% γ-mangostin by subjecting composition-I to a resin chromatography. The crude enriched extract (composition-I) was dissolved in a minimum quantity of 80% alcohol and adjusted the pH to 10-10.5 with 5% NaOH and loaded on to a resin column (styrene-divinylbenzene resin, R 20). The resin was washed with 3 column volumes of water. The desired fraction was then washed with alcohol to obtain a fraction enriched with xanthones. Evaporation of the solvent from the latter fraction yielded composition-II containing 3-isomangostin in the range of 2-4%, Garcinone C in the range of 2-4%, Garcinone D closely 0.2%, γ-mangostin in the range of 50-70%, α-mangostin in the range 0 to 4%, Deoxygartanin in the range of 1-2%, Gartanin in the range of 1.5-2.5%.

The resin for the chromatography may also be selected from one of ion exchange resins, Sephadex LH-20, any synthetic adsorbent resin. The alcohol for the resin elution may be selected from methanol, ethanol, n-propanol, isopropanol, n-butanol, isobutanol etc.

Alternatively, the demethylated mangostin composition-I is subjected to silica column chromatography using chloroform/methanol mixtures or subjected to reversed phase column chromatography over C18 or C8 silica using mixtures of water and organic solvent, wherein the organic solvent is selected from acetonitrile, acetone, methanol, ethanol, isopropanol or mixtures thereof.

The 50-70% γ-mangostin fraction from the resin column was dispersed in dichloromethane and the mixture was stirred at ambient temperature for 30 min. The insoluble solid material was filtered, washed with dichloromethane and dried under vacuum to obtain composition-III containing 3-isomangostin in the range of 0.1-2%, Garcinone C in the range of 0.1-2%, γ-mangostin in the range of 85-95%, α-mangostin in the range 0 to 1%, Deoxygartanin in the range of 0-1%, Gartanin in the range of 0-1%.

The composition enriched to contain up to 70-85% of γ-mangostin can be obtained by combining composition-II and composition-III in an appropriate ratio to obtain a desired concentration of γ-mangostin or through diluting composition-III with a natural *Garcinia mangostana* extract or an excipient.

Repeated crystallization of the composition-III in methanol/dichloromethane solvent yielded a solid containing up to 99% γ-mangostin.

The γ-mangostin compositions or the formulations containing γ-mangostin composition can be used in nutraceutical, pharmaceutical, dietary and cosmetic applications.

To obtain full benefit, it is preferable that the above mentioned γ-mangostin enriched compositions are used as it is, or the active ingredient is formulated into a solid, semi-solid or liquid dosage form by adding a conventional biologically acceptable carrier or diluent.

Specific form includes, for example, oral agents such as tablets, soft capsule, hard capsule, pills, granules, powders, emulsions, suspensions, syrups, and pellets; and parenteral agents such as injections, drops, suppositories and the like.

The following examples, which include preferred embodiments, will serve to illustrate the practice of this invention, it being understood that the particulars shown are by way of example and for purpose of illustrative discussion of preferred embodiments of the invention.

Example 1

Shade dried fruit rind (1 Kg) of *G. mangostana* was pulverized to coarse powder, and extracted with 90% methanol (5 L) for 2 hrs at 60-65° C. The solvent was separated from the raw material by filtration. Extraction process was repeated thrice using 90% methanol (3 L+3 L+2 L). The combined extracts were fine filtered and concentrated to dryness under reduced pressure to give a residue (200 g) as a dry powder (α-Mangostin: 34.2% and γ-Mangostin: 5.1%). The HPLC chromatogram is given in FIG. II.

Example 2

The 90% methanol extract of G. mangostana (100 g) diluted with 400 mL of water and extracted with ethyl acetate (3×500 mL) and combined EtOAc extracts were washed with water and dried over $Na_2SO_4$. The EtOAc extract was concentrated under vacuum to give dry powder (40 gms) containing α-Mangostin in the range of 45% and γ-Mangostin in the range of 5.5%

Example 3

The 90% MeOH extract from 500 g of G. mangostana was concentrated and adjusted pH 10-10.5 with 5% NaOH (200 mL) and loaded on to a (styrene-divinylbenzene resin R-20, 1000 mL) and washed with 3 column volumes of water. The column then eluted with 4 column volumes of methanol. The methanol fractions were combined concentrated under reduced pressure to afford a dry powder (40 gms) containing 50% α-mangostin: 50.0% and 5% γ-Mangostin by HPLC analysis.

Example 4

G. mangostana Composition Containing 25-35% γ-Mangostin $AlCl_3$ (260 g, 1.95 moles) was added in small portions over a period of 20 min to a stirred mixture of crude G. mangostana extract (140 g) in ethylene dichloride (2.8 L) and pyridine (1.05 L, 13.02 moles). Catalytic amount of sodium iodide (1 g) was added and the reaction mixture was refluxed for 2 hrs. Then the reaction mixture poured into ice-cold solution containing 3N HCl (4 L) and 2 L of brine, and extracted with THF (1×4 L, 2×3 L). The organic layer was washed with brine (2 L) and dried over anhydrous $Na_2SO_4$ and treated with triethylamine (0.4 L). The solution was concentrated to 400 g under vacuum and the crude mass was poured into 4 L of ice water. The precipitate was filtered, washed with water and dried in a vacuum oven to obtain composition-I (132 gm) enriched in γ-mangostin. The mixture shows the following composition (table 1) by HPLC analysis (FIG. III). The HPLC composition of the starting material, i.e. 90% methanol extract of G. mangostana is also summarized for comparison in table 1. The compositions containing other concentrations of γ-mangostin can be obtained by using starting material containing appropriate concentration of α-mangostin.

TABLE 1

Composition of enriched extract of Garcinia mangostana

| Name of the xanthone | Retention time (min) | Enriched extract (%) | Natural extract (%) |
| --- | --- | --- | --- |
| 3-Isomangostin (3) | 5.0 | 2.0 | 0.1 |
| Garcinone C (8) | 5.9 | 2.3 | 0.7 |
| Garcinone D (7) | 6.9 | 0.0 | 1.1 |
| γ-Mangostin (2) | 13.8 | 35.4 | 5.1 |
| Deoxygartanin (6) | 15.8 | 0.8 | 1.0 |
| Mangostinone D (4) | 18.0 | 0.2 | 0.3 |

TABLE 1-continued

Composition of enriched extract of Garcinia mangostana

| Name of the xanthone | Retention time (min) | Enriched extract (%) | Natural extract (%) |
| --- | --- | --- | --- |
| Gartanin (5) | 19.9 | 1.3 | 1.4 |
| α-Mangostin (1) | 22.3 | 1.0 | 34.2 |

Example 5

G. mangostana Composition Containing 50-70% γ-Mangostin

The crude demethylated G. mangostana extract (composition-I, 50 g) enriched in γ-mangostin as prepared in example 4 was dissolved in a minimum amount of 80% methanol. The pH was adjusted to 10-10.5 with 5% NaOH and the mixture was loaded on to a resin column (styrene-divinylbenzene resin, R 20) and washed with 3 column volumes of water. The resin column was then washed with methanol to obtain a fraction enriched with mangostins. Evaporation of the solvent from the latter fraction yielded composition-II containing 3-isomangostin 3.5%, Garcinone C 4%, Garcinone D≈0.1%, γ-Mangostin 61.5%, Deoxygartanin 1%, Gartanin 2%, α-Mangostin 2%. The compositions containing other concentrations of γ-mangostin can be obtained by using appropriate starting material.

Example 6

G. mangostana Composition Containing 85-95% γ-Mangostin

The γ-mangostin enriched fraction (≈60%, composition-II, 1.4 g) from the resin column was dispersed in dichloromethane (12 mL) and the mixture was stirred at ambient temperature for 30 min. The insoluble solid material was filtered, washed with dichloromethane and dried under vacuum to obtain composition-III (0.6 g) containing 3-isomangostin 1.0%, Garcinone C 0.4%, γ-mangostin 95%, Deoxygartanin 0.1%, Gartanin 0.3%, α-Mangostin 0.3%. The compositions containing other concentrations of γ-mangostin can be obtained by using appropriate starting material or through dilution.

Example 7

The G. mangostana fraction containing >95% γ-mangostin was achieved by crystallizing composition-III in dichloromethane/methanol mixtures. The fraction (2 g) containing 95% γ-mangostin was dissolved in 5 mL of hot methanol and the solution was diluted to 10 mL with dichloromethane. The solution was kept at room temperature for 30 min. The solid was filtered and washed with dichloromethane. The solid was dried in a vacuum oven for 2 h to obtain a pale yellow solid (m.p. 207-209° C.) containing 99.2% γ-mangostin (1.45 g).

Example 8

In-Vitro Antioxidant Activity of Garcinia mangostana

Determination of Superoxide Radical Scavenging Activity:
Superoxide radical scavenging activity of test substances was determined by the method of McCord and Fridovich (J.

Biol. Chem., 244, 6049 (1969). The assay mixture contained EDTA (6.6 mM containing 3 μg NaCN), riboflavin (2 μM), NBT (50 μM), phosphate buffer (67 mM, pH 7.8) in a final volume of 3 mL and various concentrations of test substances. The tubes were mixed well and optical densities were measured at 560 nm. The tubes were uniformly illuminated with an incandescent lamp for 15 min. and the optical densities were measured again at 560 nm. The percentage inhibition of superoxide radical generation was measured by comparing the absorbance values of control and those of the test substances. The $IC_{50}$ values were obtained from the plot drawn of the concentration (μg) verses percentage inhibition. The data are summarized in table 2.

Determination of DPPH (1,1-diphenylpicrylhydrazyl) free radical scavenging activity: DPPH free radical scavenging activity was measured by the method of Lamaison, et al., (Pharma Acta Helv. 1991; 66:185) based on the reduction of coloured methanolic solution of the DPPH. Free radical scavenging ability of each test substances added to the methanolic solution of DPPH was inversely proportional to the difference in initial and final absorption of DPPH solution at 517 nm. Antioxidant activity is expressed as the 50% inhibitory concentration ($IC_{50}$). The reaction mixture contained $1 \times 10^{-4}$ mM methanolic solution of DPPH and various concentrations of the test substances. Percentage inhibition was determined by comparing the absorbance values of test and control tubes. The $IC_{50}$ values were obtained from the plot drawn of the concentration (μg) verses percentage inhibition. The data are summarized in table 2.

TABLE 2

Antioxidant activity of *Garcinia mangostana*

| S. No | Test substance | NBT method $IC_{50}$ μg/mL | DPPH method $IC_{50}$ μg/mL |
|---|---|---|---|
| 1 | *G mangostana*, MeOH extract | 40.7 | 29.3 |
| 2 | *G mangostana*, hydroalcohol extract | 30.2 | 15.6 |
| 3 | α-Mangostin | — | >100 |
| 4 | γ-Mangostin | — | 9.7 |
| 5 | Vitamin C | 123.6 | 3.7 |

Example 9

5-Lipoxygenase Inhibitory Activity of *Garcinia mangostana* Extracts and Fractions 5-Lipoxygenase enzyme inhibitory activity was measured using the method of Schewe et al. (Adv Enzymol, Vol 58: pp 191-272, 1986), modified by Reddanna et. al., (Methods of Enzymology, Vol 187: pp 268-277, 1990). The assay mixture contained 80 μM linoleic acid and sufficient amount of potato 5-lipoxygenase in 50 mM phosphate buffer (pH 6.3). The reaction was initiated by the addition of enzyme buffer mix to linoleic acid and the enzyme activity was monitored as the increase in absorbance at 234 nm. The reaction was monitored for 120 sec and the inhibitory potential of the test substances was measured by incubating various concentrations of test substances two minutes before the addition of linoleic acid. All assays were performed three times. The IC50 values were calculated from the plot drawn of the concentrations of test substances versus percentage inhibition. The results obtained for pure standards and natural and enriched extracts are summarized in table 3.

TABLE 3

5-Lipoxygenase inhibitory activity

| S. No | Test substance | $IC_{50}$ values μg/mL |
|---|---|---|
| 1 | α-mangostin 99% | 2.7 |
| 2 | γ-mangostin 99% | 0.5 |
| 3 | Garcinone D | 5.7 |
| 4 | Garcinone C | 2.8 |
| 5 | Natural extract: α-mangostin 34%, γ-mangostin 3% | 3.82 |
| 6 | Enriched extract: α-mangostin 1%, γ-mangostin 35% | 1.5 |

Example 10

Inhibition of Tumor necrosis factor-α (TNF-α) in vitro by α-mangostin and γ-mangostin: The anti-inflammatory activities of α-mangostin, γ-mangostin and composition-I were assessed in a cell based in vitro assay. Briefly, THP-1 human monocytes cells were washed and re-suspended in phenol red free Dulbecco's Modified Eagle's Medium (DMEM) supplemented with 1% fetal Bovine serum (FBS). Equal number of cells was added to each well of a 96-well TC plate and the cells were pretreated for 2 h with various concentrations of test substances (ranging from 0.5 to 50 μg/ml; solutions prepared in culture medium from a stock solution containing 50 mg/l mL DMSO of each test compound) of α-mangostin, γ-mangostin and composition-I. The inflammatory response was induced by treatment with 100 ng/ml of LPS for 4 h at 37° C. in presence of 5% $CO_2$. The vehicle control culture wells received 0.1% DMSO in culture medium. The cell culture supernatants were collected and assessed for secretary pro-inflammatory cytokine, TNFα. The TNF-α concentration was quantitatively measured by highly specific and sensitive Enzyme Immuno Assay (EIA) kit supplied by R&D Systems, USA. The enzyme immuno assay was performed based on the protocol provided by the vendor. The inhibitory concentration for 50% inhibition (IC50) of TNF-α was determined from a plot drawn for ingredient concentration against TNF-α level. Table 4 shows a comparison of concentrations of γ-mangostin and α-mangostin for 50% inhibition of TNF-α ($IC_{50}$) in cell based in vitro model.

TABLE 4

| Compound | IC50 (μg/ml) for TNFα |
|---|---|
| γ-mangostin | 3.322 |
| α-mangostin | >20.0 |
| Composition-I | 5.136 |

Example 11

Down-Regulation of aP2 Protein Expression by γ-Mangostin and α-Mangostin in Human Monocytes-Macrophage Cells Down-regulation of aP2 protein expression by α-mangostin and γ-mangostin was evaluated in a cell based in vitro model. Briefly, equal number of THP-1 monocyte cells was plated in 40 mm tissue culture petri-dishes and the cells were differentiated to macrophages by treatment with 10 nM Phorbol myristate acetate (PMA) for 24 h. The attached cells in the culture dishes were washed with serum free and phenol red free DMEM; and the differentiated macrophage cells were pre-treated for 2 h with either 5 µg/ml of γ-mangostin or α-mangostin or 0.1% DMSO in serum free DMEM supplemented with 2% BSA. Thereafter, the cells were primed with 100 ng/ml of LPS for 16 h to induce the inflammatory response. The 0.1% DMSO treated cells without LPS treatment were considered as vehicle control. The cellular proteins were extracted by cell lysis buffer (50 mM Tris-HCl, pH 7.5, 150 mM NaCl, 1% Triton X-100, Sodium deoxycholate 0.5%, and a protease inhibitor cocktail). The protein content was measured by Coomassie blue based Bradford method and equal amount of cellular protein lysates (2 µg) was resolved in 15% SDS-Polyacrylamide gels. The resolved proteins were electro-blotted onto nitrocellulose membranes and probed with 1:2000 dilution of anti-aP2 antibody (R&D Systems, USA), overnight. The aP2 protein expression was specifically detected by chemiluminescent substrate (Pierce, USA); detection of chemiluminescent bands and densitometric analyses were carried out on Kodak 4000 mM image station (supplied by Kodak, USA). The same nitrocellulose blots were stripped and re-probed with anti-actin antibody (Sigma Chemical CO, USA) and actin protein expression was recorded as an indication of equal protein loading in each lane. The aP2 protein expression was normalized with the actin expression in respective samples. FIG. IV represents immuno-western blot showing inhibition of aP2 protein expression by α- and γ-mangostin in LPS induced THP-1 human monocyte derived macrophage cells. The γ-mangostin was found to be more potent inhibitor of aP2 in vitro compared to α-mangostin.

Example 12

Anti-Asthma Activity of Composition-I as Indicated by Down-Regulation of Pro-Inflammatory Modulators in Sephadex LH-20 Induced Airway Inflammation in Sprague-Dawley Rats Selected healthy Sprague-Dawley rats were randomly assigned to control or various treatment groups (n=6). The study protocol includes saline (vehicle) inoculated control group (1), Sephadex inoculated airway inflammation induced asthma control group, which received no treatment (2), Sephadex inoculated air way inflammatory asthma treatment group, which received treatment with Composition-I (3). The treatment group rats were supplemented with composition-I at 50 mg/kg per day for 10 days. Thereafter, vehicle (saline, 1 ml/kg) or Sephadex LH-20 (5 mg/kg) was inoculated via intratracial route. Sephadex was prepared as a suspension by soaking in sterile saline for 3 days prior to inoculation. Animals were sacrificed 24 h after saline or Sephadex challenge. The blood and lung tissue samples were collected from respective animals. Pro-inflammatory cytokines such as TNFα and IL-4 were measured quantitatively in blood serum and protein lysates prepared from lung tissues by specific antibody coated ELISA plates, by adopting the protocol supplied by the vendor (R&D Systems, USA). The data is summarized in FIG. V.

The above in vivo experimental studies suggest that γ-mangostin or the compositions enriched in γ-mangostin possess potential application for the prevention and inhibition of free radical, TNF-α, aP2 and 5-lipoxygenase mediated diseases such as inflammation or asthma.

Example 13

Antibacterial activity of enriched compositions: The antibacterial activity of composition-I was determined by Agar cup-plate (Cup dia 8 mm) against the microorganisms *Bascillus subtilis, S. epidermidis* and *S. aureus*. The minimum inhibitory concentrations (MIC) of composition-1 against these organisms were found to be 3 mcg/mL, 2 mcg/mL and 2 mcg/mL respectively.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A process for producing a composition with antibacterial activity, comprising an enriched *Garcinia mangostana* extract, said process comprising the step of:
    a) demethylating a hydroalcoholic extract of a fruit pericarp (fruit hull) of *Garcinia mangostana* in an organic solvent, wherein said hydroalcoholic extract comprises α-mangostin and minor amounts of other xanthones,
    said demethylating being performed in the presence of a Lewis acid, an organic base, and a catalyst to yield composition-I enriched in demethylated xanthones,
    wherein said composition-I comprises γ-mangostin in the range of 20% to 40% of total weight of composition-I, α-mangostin in the range of 0 to 3%, garcinone C in the range of 0.5 to 3% and 3-isomangostin in the range of 0.5 to 2.5%.

2. The process as claimed in claim 1, wherein said Lewis acid used in said demethylating step is selected from the group consisting of aluminum chloride, aluminum bromide, aluminum iodide, boron tribromide, a boron trichloride-methyl sulfide complex, a sodium salt of N-methylaniline, sodium ethanethiolate, lithium chloride, beryllium chloride in dimethyl formamide, and a mixture thereof.

3. The process as claimed in claim 1, wherein the catalyst used in said demethylating step is an alkali metal iodide, magnesium iodide, calcium iodide, or a phase transfer catalyst.

4. The process as claimed in claim 1, wherein said composition-I is subjected to column chromatography to yield composition-II enriched in γ-mangostin in the range of about 50 to 70%.

5. The process as claimed in claim 1, wherein said composition-I is subjected to silica gel/reversed phase flash column chromatography to yield composition-II enriched in γ-mangostin in the range of about 50 to 70%.

6. The process as claimed in claim 4, wherein said composition-II is subjected to:
    column chromatography over silica/reversed phase silica, and then
    crystallization to yield composition-III comprising γ-mangostin in the range of 85-95%.

7. The process as claimed in claim 6, further comprising a step of recrystallizing said composition-III repeatedly in methanol/dichloromethane solvent to obtain a solid containing up to 99% γ-mangostin.

8. The process as claimed in claim 4, wherein subjecting said composition-I to column chromatography comprises:

dissolving said composition-I in an aqueous organic solvent and adjusting the pH to 10-10.5 with alkali solution, followed by subjecting the solution of composition-I to a column chromatography by depositing the solution on a styrene-divinylbenzene resin column, eluting the column with water, followed by eluting the column with an organic solvent to obtain an organic fraction, and evaporating the organic solvent from the organic fraction to obtain composition-II, wherein said composition-II comprises γ-mangostin in the range of 50% to 70% of the total weight of composition-II, α-mangostin in the range of 0 to 4%, garcinone C in the range of 0.5 to 4% and 3-isomangostin in the range of 0.5 to 4%.

9. The process as claimed in claim 8, wherein said aqueous organic solvent contains an organic solvent selected from the group consisting of acetone, ethyl acetate, methanol, ethanol, isopropanol, and mixtures thereof.

10. The process as claimed in claim 8, wherein said organic solvent used in said eluting is selected from the group consisting of acetone, ethyl acetate, methanol, ethanol, isopropanol, and mixtures thereof.

11. The process as claimed in claim 4, wherein said Composition-II is dispersed into dichloromethane, followed by stirring the dichloromethane solution for 30 min, followed by filtration of insoluble solid material, and drying the insoluble solid material under vacuum to obtain composition-III;

wherein said composition-III comprises γ-mangostin in the range of 85% to 95% of the total weight of composition-III, α-mangostin in the range of 0 to 1%, garcinone C in the range of 0.1 to 2% and 3-isomangostin in the range of 0.1 to 2%.

* * * * *